(12) United States Patent
Zappala

(10) Patent No.: US 6,648,872 B1
(45) Date of Patent: Nov. 18, 2003

(54) CIRCUMFERENTIAL COMPRESSION DEVICE FOR INTRACAVERNOSAL ANESTHESIA AND METHOD FOR USING SAME

(76) Inventor: Stephen M. Zappala, 98 Rattlesnake Rd., Andover, MA (US) 01810

( * ) Notice: Subject to any disclaimer, the term of this patent is extended or adjusted under 35 U.S.C. 154(b) by 0 days.

(21) Appl. No.: 09/656,050

(22) Filed: Sep. 6, 2000

Related U.S. Application Data

(60) Provisional application No. 60/152,718, filed on Sep. 7, 1999.

(51) Int. Cl.[7] .......................... A61M 31/00; A61K 9/00; A61F 13/00; A61F 2/00
(52) U.S. Cl. ..................... 604/500; 604/517; 424/422; 424/423; 424/400
(58) Field of Search ................................ 424/422, 423, 424/400; 600/38, 41; 604/517, 500

(56) References Cited

U.S. PATENT DOCUMENTS 5,085,209 A * 2/1992 Gottschalk ................. 600/41

OTHER PUBLICATIONS

Taber's Cyclopedic Medical Dictionary p. 2014.*

Pertek et al Penile Blcok in Adults Ann. Fr. Anesth. Reanim. 11(1):82–87 1992.*

* cited by examiner

*Primary Examiner*—Thurman K. Page
*Assistant Examiner*—Todd D Ware
(74) *Attorney, Agent, or Firm*—Jenifer E. Haeckl, Esq.; Mirick, O'Connell, DeMallie & Lougee, LLP

(57) ABSTRACT

A preferred embodiment of the device of the invention, which is adapted to be applied circumferentially about a phallus, having a perimeter, and to facilitate intracavernosal anesthesia, generally comprises: a strip having a length at least slightly greater than the perimeter of the phallus, and a first end and a second end; and a hook and loop closure for releasably fixing at least a portion of the strip proximate the first end to a second portion of the strip

3 Claims, 2 Drawing Sheets

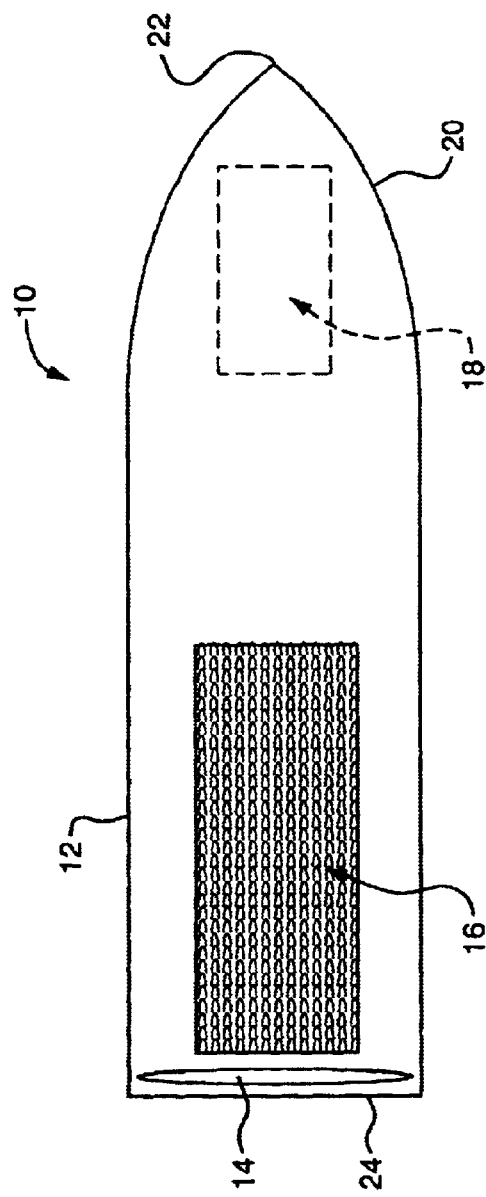
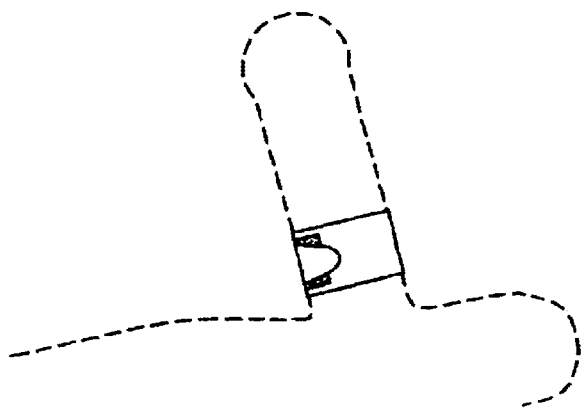
FIG. 2
FIG. 1

CIRCUMFERENTIAL COMPRESSION DEVICE FOR INTRACAVERNOSAL ANESTHESIA AND METHOD FOR USING SAME

This application claims the benefit of provisional application 60/152,718 filed Sep. 7, 1999.

FIELD OF THE INVENTION

This invention relates to devices used for administering anesthesia for penile surgery and more specifically to a circumferential compression device that facilitates intracavernosal anesthesia.

BACKGROUND OF THE INVENTION

For various types of ambulatory penile surgery, including circumcision, penile biopsy, partial penectomy and cystoscopy, a penile regional anesthetic nerve block is administered. To administer the anesthetic nerve block, a conventional tourniquet is applied to the phallus before injecting the anesthetic into the corpus cavernosum. Although the regional anesthetic is preferred for ambulatory urologic surgery over spinal or inhalation anesthesia, various surgical complications are associated with conventional tourniquet techniques including, neuropraxia, vascular thrombosis, and compression injury to the corpus cavernosum. Such complications arise, in part, because it is difficult to achieve a uniform amount of compression with a conventional tourniquet.

SUMMARY OF THE INVENTION

It is therefore a primary object of this invention to provide an adjunct device for intracavernosal anesthesia that achieves a more uniformly applied amount of compression than conventional tourniquets.

It is a further object of this invention to provide a circumferential compression device that is safe and effective and achieves reproducible anesthetic for ambulatory penile surgery.

It is a further object of this invention to provide a method and device for administering intracavernosal anesthesia that does not distort the penile anatomy and obviates potential risks and financial considerations associated with inhalation and spinal anesthesia.

It is a further object of the invention to provide a novel penile block that incorporates the post-operative analgesic benefits of preemptive analgesia.

It is a further object of the invention to provide a method and device for intracavernosal anesthesia that does not produce cardiac arrhythmias, central nervous system disturbances or plaque formation at the injection site.

It is a further object of the invention to provide a device and method for intracavernosal anesthesia that distributes a variable amount of desired tension in a more uniform manner than a standard tourniquet.

It is a further object of the invention to provide a device and method for intracavernosal anesthesia that decreases the potential for neuropraxia, vascular thrombosis and compression injury to the corpus cavernosum.

A preferred embodiment of the device of the invention, which is adapted to be applied circumferentially about a phallus, having a perimeter, and to facilitate intracavernosal anesthesia, generally comprises: a strip having a length at least slightly greater than the perimeter of the phallus, and a first end and a second end; and a means for releasably fixing at least a portion of the strip proximate the first end to a second portion of the strip. Wherein the strip may further comprise one or more openings through the strip that is adapted to receive the first end through one or more of the openings. The strip may also have a width proximate the second end and a width proximate the first end that is smaller than the width proximate the second end. The strip preferably has an inner surface, wherein the strip may further comprise one or more cushioning means fixed to at least a portion of the inner surface, wherein one or more of the cushioning means may comprise foam padding. At least a portion of the strip preferably tapers somewhat proximate the first end.

The means for fixing may comprise one or more hooks and loops, and more specifically, may comprise, an adjustable, releasable hook and loop closure, comprising a hook means and a loop means, wherein the hook means is fixed to the second portion of an outer surface of the strip and the loop means is fixed to the first portion of the outer surface of the strip proximate the first end.

Another preferred embodiment of the device of the invention which is adapted to be applied circumferentially about a phallus, having a perimeter, to facilitate intracavernosal anesthesia, generally comprises: a strip having a length at least slightly greater than the perimeter of the phallus, comprising, a first end, a second end and an inner surface; one or more cushioning means fixed to at least a first portion of the inner surface; and one or more openings through the strip that is adapted to receive the first end through one or more of the openings; and one or more means for releasably fixing at least a first portion of the strip proximate the first end to a second portion of the strip; wherein the means for fixing comprises an adjustable, releasable hook and loop closure, comprising at least one hook means and at least one loop means, wherein the hook means is fixed to at least the second portion of an outer surface of the strip and the loop means is fixed to the first portion of the outer surface of the strip proximate the first end.

The preferred method of the invention for facilitating the administration of anesthesia to a corpus cavernosum of a phallus, having a perimeter, generally comprises the steps of: providing a strip having a length that is at least slightly greater than the perimeter of the phallus, comprising, a first end, a second end and an inner surface; one or more openings through the strip that is adapted to receive the first end through one or more of the openings; and one or more adjustable means for releasably fixing at least a first portion of the strip proximate the first end to a second portion of the strip: wrapping the strip about the phallus: inserting the first end of the strip through one or more of the openings: fixing at least a portion of the strip proximate the first end to the second portion of the strip using the means for fixing: and instilling the anesthesia using a needle into the corpus cavernosum. The strip may further comprise one or more cushioning means fixed to at least a portion of the inner surface; and wherein the strip is wrapped about the phallus so that the cushioning means is between the inner surface of the strip and the phallus.

BRIEF DESCRIPTION OF THE DRAWINGS

Other objects, features and advantages will occur to those skilled in the art from the following description of the preferred embodiments and the accompanying drawings in which:

FIG. 1 is a side view of the preferred embodiment of the device of this invention employed in a surgical position;

FIG. 2 is a front view of the outer side of the device of FIG. 1 when not in use;

DETAILED DESCRIPTION OF THE PREFERRED EMBODIMENTS

The invention features a circumferential, external device that provides gentle compression at the base of the phallus during the technique of intracavernosal anesthesia. The device includes a foam-cushioned, inner surface that distributes a variable amount of desired tension in a more uniform manner than a standard tourniquet. The larger field of pressure distribution decreases potential surgical complications such as neuropraxia, vascular thrombosis, and compression injury to the corpus cavernosum that are associated with conventional tourniquet techniques. The device further provides more patient comfort while applying circumferential tension, and enhances the clinical outcomes by employing the preferred methods of the invention. The device is preferably single use and disposable and can be produced in various sizes to accommodate newborn, pediatric and adult populations.

The device features an inserting tab mechanism and a self-locking Velcro® strip on its outer surface that allows the surgeon to deliver variable compression pressures. The device is applied around the phallus and the correct tension is generated. The tension is maintained by securing the Velcro® strip back upon itself in a standard manner. The device is removed from the phallus, after suitable anesthesia is attained, by disengaging the Velcro ® strip. The circumferential pressure is thus released by disengaging the Velcro®.

Figure 3:
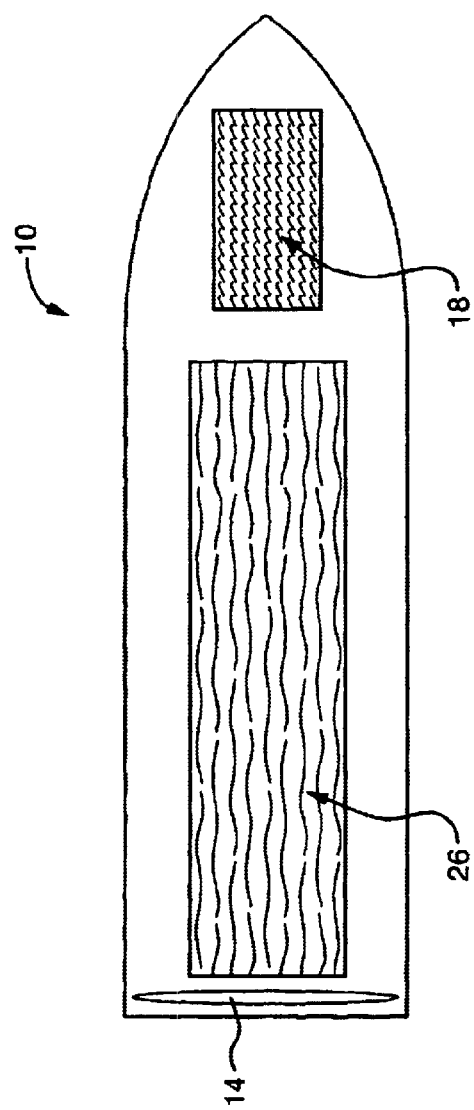
FIG. 3 is a front view of the inner side of the device of FIG. 1 when not in use.

The preferred embodiment of the device of the invention is shown in FIGS. 1–4 and referred to as device 10. Device 10 generally comprises: strip 12; reinforced opening 14; a two-part means on the outer surface of strip 12 (e.g. hook means 16 and loop means 18) for releasably fixing the first, or distal, portion 20 of the strip to the second, or proximal, portion of the strip; and cushioning means 26 provided on the inner surface of strip 12. The width of strip 12 should be optimized to provide the most uniform compression when in use. The width of strip 12 should be constant over most of its length to provide uniform compression and then preferably tapers down, as shown in FIG. 3, to rounded tip 22 over distal portion 20. For example, for adult patients, the width of strip 12 is preferably about 4 cm for most of the length of strip 12 until strip 12 begins to taper down.

One or more cushioning means 26 are fixed to the inner surface of strip 12 to provide a cushion between strip 12 and the phallus of the patient. Cushioning means 26 is preferably a foam padding, although other suitable cushioning materials may be used in addition to the foam or as an alternative to the foam. The cushioning means may be fixed to strip 12 by any means suitable for surgical applications. Cushioning means preferably extends along the entire portion of strip 12 which is adapted to surround a phallus in a single layer and which has a uniform width along its length. The cushioning means preferably does not extend along the tapered portion of strip 12 that will likely be pulled through opening 14.

Figure 4:
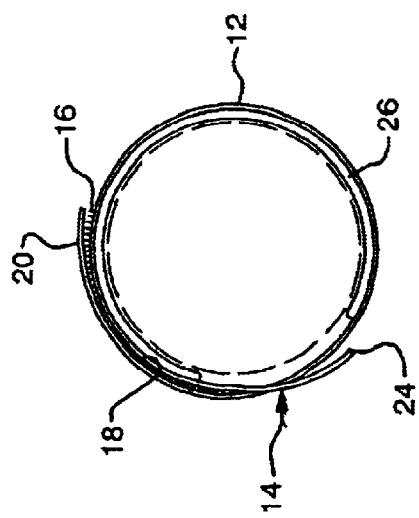
FIG. 4 is cross-sectional view of the device in use.

The means for fixing may comprise one or more hooks and loops, and more specifically, may comprise, an adjustable, releasable hook and loop closure, comprising a hook means 16 and a loop means 18. One type of hook and look closure suited to the device is commonly known as Velcro®. The hook means is preferably fixed to the outer surface of strip 12 near the second, proximal end of strip 12 and the loop means is preferably fixed to the outer surface of the first portion 20 of strip 12. The means for fixing may be fixed to strip 12 by any fixation means suitable for surgical applications. The hook means and loop means must be positioned on strip 12 so that, after device 10 is wrapped around a phallus and end 22 is inserted through opening 14, loop means 18, as fixed on portion 20, can be folded back over proximal end 24 of strip 12 and pressed against hook means 16 so that device 10 is held as snugly, as adjusted by the surgeon, around the phallus to achieve a uniform compression, as shown in FIG. 4. Hook means 16 and loop means 18 can be interchangeably positioned on strip 12. The length of strip 12 and the position and length of hook means and loop means is dependent on the type of patient, e.g. newborn, pediatric or adult. For example, the total length of strip. 12 for an adult would be about 15 cm.

Opening 14 is preferably a slot that is wide enough to allow end 22 and at least part of tapered portion 20 of strip 12 to be inserted and pulled through opening 14 so that end 22 can be folded back over end 24 and loop means 18 pressed against hook means 16. Depending on the material used to fabricate strip 12, the edges of opening 14 should be reinforced to prevent end 24 from splitting.

The preferred method of the invention for facilitating the administration of anesthesia to a corpus cavernosum of a phallus, having a perimeter, generally comprises the steps of: providing a strip such as strip 12; wrapping the strip about the phallus so that the cushioning means lays against the outer surface of the phallus; inserting the first end 22 of strip through opening 14; fixing the distal portion 20 of strip 12 to the proximal portion of strip 12 by pressing loop means 18 against hook means 16. Once strip is fixed snugly, or as needed, about the patient's phallus, the anesthesia is instilled, using a needle, into the corpus cavernosum.

The method of the invention is specifically used to facilitate the administration of a penile regional anesthetic nerve block prior to urologic surgery. The method features the intracavernosal instillation of lidocaine HCl 1% (Abbott Laboratories, North Chicago, Ill.) and bupivacaine HCl 0.25% (Astra, Westborough, Mass.). Adequate analgesia is achieved rapidly using the method and provides an attractive alternative to spinal or inhalation anesthesia. The method eliminates the phallic distortion associated with subcutaneous dorsal nerve infiltration and incorporates the benefits of preemptive analgesia, and thus reduces post-operative pain and the need for narcotic therapy.

The device of the invention is preferably applied at the midshaft of the phallus and a #21 gauge butterfly needle is introduced into the right cavernosal body. The gentle aspiration of desaturated blood will verify the correct needle position within the corpus cavernosum. Ten cubic centimeters (cc) of 0.25% bupivacaine are combined with 20 cc of 1% lidocaine for a total volume of 30 cc. An artificial penile erection is created as 30 cc of the solution is slowly instilled. Total anesthesia is achieved approximately five minutes after instillation. The device is then removed to obtain hemostasis.

By using the device and method of the invention, conversion to general anesthesia is usually not required and intraoperative or post-operative bleeding is insignificant. At most, acetaminophen may be used as post-operative analgesia. Surgical complications, such as cardiac arrhythmias, central nervous system disturbances, plaque formation at the injection site and penile anatomy distortion are non-existent.

The device and method provide a safe, effective and reproducible anesthetic for intracavernosal infiltration of lidocaine/bupivacaine for ambulatory penile surgery and further incorporates the post-operative analgesic benefits of preemptive analgesia.

Although specific features of the invention are shown in some drawings and not others, this is for convenience only as some feature may be combined with any or all of the other features in accordance with the invention.

Other embodiments will occur to those skilled in the art and are within the following claims.

What is claimed is:

1. A method for administering anesthetic to a corpus cavernosum of a phallus, having a perimeter, comprising the steps of,
    providing a strip having a length that is at least slightly greater than said perimeter of said phallus comprising,
    a first end, a second end and an inner surface;
    one or more openings through said strip that is adapted to receive said first end through one or more of said openings,
    one or more adjustable means for releasably fixing at least a first portion of said strip to proximate said first end to a second portion of said strip; and
    one or more cushioning means fixed to at least a first portion of said inner surface;
    wrapping said strip about said phallus;
    inserting said first end of said strip through one or more of said openings,
    fixing at least a portion of said strip proximate said first end to said second portion of said strip using said means for fixing; and
    instilling said anesthetic using a needle into said corpus cavernosum;
    wherein the step of instilling said anesthetic comprises, applying said anesthetic at the midshaft of the phallus by introducing said needle into a right cavernosal body of said phallus, wherein said anesthetic comprises 0.25% bupivacaine and 1% lidocaine.

2. The method of claim 1, wherein said anesthetic comprises about 30 cc of a combination of said 0.25% bupivacaine and said 1% lidocaine.

3. The method of claim 1, wherein said anesthetic comprises 10 cc of 0.25% bupivacaine and 20 cc of 1% lidocaine.

* * * * *